US011383060B2

(12) United States Patent
Wruck (10) Patent No.: US 11,383,060 B2
(45) Date of Patent: Jul. 12, 2022

(54) DEVICE AND METHOD FOR DISPENSING AN ANESTHETIC INTO A GAS STREAM

(71) Applicant: Drägerwerk AG & Co. KGaA, Lübeck (DE)

(72) Inventor: Norbert Wruck, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 457 days.

(21) Appl. No.: 15/318,474

(22) PCT Filed: Jun. 2, 2015

(86) PCT No.: PCT/EP2015/001122
§ 371 (c)(1),
(2) Date: Dec. 13, 2016

(87) PCT Pub. No.: WO2015/192946
PCT Pub. Date: Dec. 23, 2015

(65) Prior Publication Data
US 2017/0151412 A1 Jun. 1, 2017

(30) Foreign Application Priority Data
Jun. 17, 2014 (DE) ...................... 10 2014 008 625.9

(51) Int. Cl.
*A61M 16/18* (2006.01)
*A61M 16/10* (2006.01)

(52) U.S. Cl.
CPC .......... *A61M 16/18* (2013.01); *A61M 16/104* (2013.01); *A61M 16/108* (2014.02); *A61M 2205/3368* (2013.01); *A61M 2205/36* (2013.01)

(58) Field of Classification Search
CPC .. A61M 16/00; A61M 16/01; A61M 16/1045; A61M 16/10; A61M 16/104;
(Continued)

(56) References Cited

U.S. PATENT DOCUMENTS

| 3,671,024 A | * | 6/1972 | Breiling | A61M 16/18 |
| | | | | 128/203.14 |
| 3,836,129 A | * | 9/1974 | Perelmutr | A61M 16/18 |
| | | | | 128/203.25 |

(Continued)

FOREIGN PATENT DOCUMENTS

| CN | 1246372 A | 3/2000 |
| CN | 101780302 A | 7/2010 |

(Continued)

OTHER PUBLICATIONS

Shaffer, Philip A., and Ethel Ronzoni. "Ether Anesthesia: The Determination of Ethyl Ether in Air and in Blood, and its Distribution Ration between Blood and Air". (1923). Elsevier Inc, vol. 57, issue 3, pp. 741-760. (Year: 1923).*

*Primary Examiner* — Rachel T Sippel
*Assistant Examiner* — Jacqueline M Pinderski
(74) *Attorney, Agent, or Firm* — McGlew and Tuttle, P.C.

(57) ABSTRACT

A device, for dispensing an anesthetic into a gas stream, has a gas inlet, via which gas to be enriched with anesthetic and coming from a gas source flows in and with a gas outlet, via which gas enriched with anesthetic flows out to a patient port. A heating element, for heating the gas stream, is arranged upstream of an evaporation chamber, for dispensing an anesthetic into the gas stream, between the gas inlet and the gas outlet. The heating element is actuated by a control unit such that heat is fed to the gas to be enriched with anesthetic for evaporation of the anesthetic located in the evaporation chamber as a function of at least one status parameter of the gas to be enriched with the anesthetic and/or of the gas at least partially enriched with the anesthetic.

20 Claims, 4 Drawing Sheets

(58) Field of Classification Search
CPC .......... A61M 16/14; A61M 16/18; A61M 16/1075–108; A61M 2205/3368; A61M 2205/36; A61M 2205/3613; A61M 2016/1035

See application file for complete search history.

(56) References Cited

U.S. PATENT DOCUMENTS

| | | | | |
|---|---|---|---|---|
| 4,477,395 | A | * 10/1984 | Albarda | A61M 16/147 |
| | | | | 261/131 |
| 4,484,576 | A | 11/1984 | Albarda | |
| 4,587,966 | A | * 5/1986 | Albarda | A61M 16/18 |
| | | | | 128/202.22 |
| 6,672,306 | B2 | 1/2004 | Loser | |
| 7,992,554 | B2 | 8/2011 | Radomski | |
| 2002/0157670 | A1 | * 10/2002 | Kullik | A61M 16/18 |
| | | | | 128/203.12 |
| 2008/0105257 | A1 | 5/2008 | Klasek et al. | |
| 2011/0000488 | A1 | * 1/2011 | Blomberg | A61M 16/01 |
| | | | | 128/203.14 |

FOREIGN PATENT DOCUMENTS

| | | | |
|---|---|---|---|
| DE | 31 16 951 A1 | 12/1982 | |
| DE | 32 34 474 A1 | 3/1984 | |
| DE | 41 05 858 A1 | 8/1992 | |
| DE | 4105858 A1 * | 8/1992 | .......... A61M 16/18 |
| GB | 2239806 A * | 7/1991 | .......... A61M 16/18 |
| WO | 2004/091708 A2 | 10/2004 | |

\* cited by examiner

$$\dot{Q}_{11} = \dot{m}_{11} * c_{p_{11}} * \vartheta_{11}$$

IN WHICH $$\vartheta_{11} = \frac{1}{\dot{m}_{11} * c_{p_{11}}} * \left[ \dot{m}_{VA} * (c_{pVA,d} * \vartheta_{15} + r_0 - c_{fl} * \vartheta_{13}) + \dot{m}_{11} * c_{p_{11}} * \vartheta_{15} \right]$$

$\dot{m}$ = MASS FLOW $c$ = SPECIFIC HEAT CAPACITY $\vartheta$ = TEMPERATURE IN DEGREES CELSIUS $r_0$ = SPECIFIC EVAPORATION ENTHALPY $\dot{Q}$ = HEAT FLOW WITH $\vartheta_{Ref.} = 0\,°C$

FIG 4

DEVICE AND METHOD FOR DISPENSING AN ANESTHETIC INTO A GAS STREAM

CROSS REFERENCE TO RELATED APPLICATIONS

This application is a United States National Phase Application of International Application PCT/EP2015/001122 filed Jun. 2, 2015, and claims the benefit of priority under 35 U.S.C. § 119 of German Application 10 2014 008 625.9 filed Jun. 17, 2014, the entire contents of which are incorporated herein by reference.

FIELD OF THE INVENTION

The present invention pertains to a device as well as to a method for dispensing an anesthetic into a gas stream. A dispensing device of this class has between the gas inlet and the gas outlet an evaporation chamber, in which an anesthetic can be added to the gas stream at least occasionally, and further has a heating element, which heats the gas at least occasionally.

BACKGROUND OF THE INVENTION

A plurality of anesthesia apparatuses are known from the state of the art, with which an anesthetic is fed to a breathing gas stream for a patient for the occasional anesthetization of the patient ventilated by the anesthesia apparatus during this time. In this connection, predominantly mechanically operating anesthetic evaporators are still used for enriching the breathing gas stream with volatile anesthetics. Such apparatuses, which operate according to the stream splitter principle, are characterized by their reliability and are hence widely accepted. Nevertheless, the problem with these apparatuses is that comparatively high thermal storage masses have to be used to prevent the apparatus from cooling down during the demand of high evaporation mass flows, and thus, an unallowable drop in the vapor pressure and hence in the desired vapor-discharge capacity would occur. Because of the required thermal storage masses, mechanically operating anesthetic evaporators are often relatively heavy, which is in turn a drawback for handling.

As an alternative to the anesthetic evaporators mentioned above, high-output electronic evaporators are known, as they are described, for example, in DE 31 16 951 A1. These anesthetic evaporators, which have a high vapor-discharge capacity, operate with pressurized anesthetic and thus require a comparatively complicated safety technology. A plurality of sensor mechanisms and actuator mechanisms are hence necessary to ensure a sufficient safety of the apparatuses, which in turn has a negative effect on the costs for such apparatuses and the failure rate thereof.

Further, an anesthetic evaporator, in which the anesthetic flow is set based on need by means of a proportional valve operated in a controlled manner, is known from WO 2004/091708. In this case, the control is based on a fresh gas measurement and a closed control circuit on the liquid side. The anesthetic evaporator described has an evaporation chamber, which is connected to the fresh gas stream, wherein a heating element, by means of which an evaporation of the liquid anesthetic based on need is ensured, is provided within the evaporation chamber. A drawback of this system, which operates fully electronically, is the high cost for the required sensor mechanism or actuator mechanism.

SUMMARY OF THE INVENTION

Based on the known technical solutions for dispensing an anesthetic into a breathing gas stream, a basic object of the present invention is to perfect a corresponding system such that, on the one hand, the discharge of even large quantities of vapor is possible, and, on the other hand, the structural and control-related cost is comparatively low. The device to be specified shall especially have only minimal sensor technology as well as few adjusting elements, so that a lightweight, fail-safe, cost-effective and yet high-output anesthetic dispensing is achieved. It is essential in this case that the goal be reached without the volatile anesthetics used being exposed to an unallowable thermal load. At the same time, the safety-related and economic drawbacks of pressurized systems on anesthetic dispensing shall be ruled out.

According to the present invention, a device is provided for dispensing an anesthetic into a gas stream. A gas to be enriched with anesthetic is fed in from a breathing gas source and flows in via a gas inlet. The gas, enriched with the anesthetic, flows out via a gas outlet to a patient port. An evaporation chamber, in which an anesthetic is added to the gas stream at least occasionally, and a heating element, for the heating of the gas at least occasionally, are arranged in the flow direction of the gas between the gas inlet and the gas outlet. The heating element is arranged in front of the evaporation chamber in the flow direction of the gas and is actuated by a control unit such that heat is fed to the gas to be enriched with anesthetic for evaporation of the anesthetic located in the evaporation chamber as a function of at least one status parameter of the gas to be enriched with anesthetic and/or of the gas enriched with the anesthetic at least occasionally.

The essential idea of the present invention is thus based on a novel embodiment of the passive evaporator principle, wherein the heat required for the evaporation of the anesthetic, located in the anesthetic evaporator, is introduced based on need, quasi indirectly into the evaporation chamber, namely via the gas stream entering the evaporation chamber and to be enriched with anesthetic. The introduction of the necessary heat into the gas stream to be enriched with anesthetic in this case takes place as a function of at least one status parameter or one thermodynamic status variable of the gas stream located in the flow direction in front of, in and/or behind the evaporation chamber. The heat output is preferably controlled taking into consideration the temperature and/or the material composition of the gas stream. In this case, a closed control circuit is especially preferably generated, wherein a settable value of the at least one status parameter of the gas stream located in front of, in and/or behind the evaporation chamber represents the command variable and the respectively necessary heat output represents the control variable.

In a special embodiment of the present invention, the heating element is actuated as a function of a required quantity of anesthetic after leaving the evaporation chamber. In this case, so much heat is fed to the gas stream to be enriched with anesthetic before entry into the evaporation chamber that a gas stream enriched with anesthetic leaves the evaporation chamber, in which the anesthetic has a predefined or desired concentration and quantity of anesthetic.

According to a special embodiment of the present invention, the heating element can be actuated so that heat is fed to the gas to be enriched with anesthetic for evaporation of the anesthetic located in the evaporation chamber as a function of a required desired concentration of anesthetic in the gas and/or of a necessary anesthetic volume flow after leaving the evaporation chamber. In this case, the heating element is preferably actuated taking into consideration a gas volume flow of the gas stream flowing in the dispensing duct in front of and/or behind the evaporation chamber.

According to a special variant, it is determined from the respective gas volume flow, the necessary desired concentration and/or the necessary anesthetic volume flow as well as the thermodynamic material values of the volatile anesthetic, for example, specific evaporation enthalpy and specific heat capacity, which heat flow has to be fed to the evaporation chamber in the respective operating state. The control is thus based on an energy-process-engineering-based balancing in terms of mass and enthalpy. The gas to be enriched with anesthetic preferably comes from a gas mixer of an anesthesia apparatus, the gas mixer used being advantageously controlled electronically. In a special embodiment, so much heat is fed to the gas stream to be introduced into the evaporation chamber that the gas stream leaving the evaporation chamber is saturated with anesthetic. A later reduction of the anesthetic concentration is achieved in this case as needed by a suitable admixture of fresh gas.

It is essential in any case that the evaporation enthalpy be fed based on need to the liquid, volatile anesthetic located in the evaporator by heating the gas stream to be enriched with anesthetic and the subsequent cooling off proceeding independently in the evaporation chamber during the evaporation process. The feeding of the heat required in the respective state takes place in this case in a fluid-borne manner, i.e., by means of the heated gas, which was taken from a gas source. A special advantage of this form of heat feeding is that the evaporation chamber can have a comparatively lightweight configuration, since it only has to have low thermal masses by contrast to the solutions known from the state of the art.

According to a special embodiment of the present invention, the evaporation chamber has a tank for liquid anesthetic and an evaporation area, in which liquid anesthetic evaporates at least partly during the operation. The tank and evaporation area are preferably configured as one component, which can be called an anesthetic evaporator. In this connection, it is preferable that such a component or anesthetic evaporator has at least one suitable fastening element for the detachable connection to an anesthesia apparatus. The provision of such a fastening element ensures that an anesthetic evaporator can be removed from an anesthesia apparatus in a relatively simple manner for cleaning, maintenance or filling with anesthetic and can be reattached to this anesthesia apparatus after completion of the operations carried out. Of course, it is hereby likewise possible in a simple manner to replace a correspondingly equipped anesthetic evaporator with one having a structurally identical configuration.

Moreover, provisions are made in a special embodiment for the heating element, which is arranged upstream of the evaporation chamber in terms of the flow, to be configured as a structurally unified component together with the evaporation chamber. An outer wall of the evaporation chamber is preferably shaped for this such that the heating element is accommodated within the recess formed by the outer wall, which recess is preferably half open. The heating element advantageously has at least one fastening element, with which this element can be at least indirectly fastened to the outer wall of the evaporation chamber.

In a special variant of the present invention, the heating element and the evaporation chamber are arranged in terms of flow parallel to a fresh gas duct, wherein the two partial gas streams flowing through the fresh gas duct, on the one hand, and the evaporation chamber, on the other hand, are merged in a mixing point in front of a patient connector. Thus, according to this embodiment, on the one hand, a dispensing duct, in which the heating element and the evaporation chamber are arranged in series and, on the other hand, a fresh gas duct arranged parallel to the dispensing duct in terms of flow, are provided, through which the two partial gas streams are fed based on need.

According to another embodiment, the heating element may be actuated such that the temperature of a chamber wall defining the evaporation area of the evaporation chamber in at least some areas remains at least almost constant during the operation. In the stationary operating state, a determination of the temperature difference between the gas stream flowing into the evaporation chamber and the anesthetic liquid located there thus takes place based on need. For the control of the heating element, i.e., for determining the heat required in the evaporation chamber, the quantity, especially the volume flow, as well as the temperature of the gas stream to be enriched with the anesthetic are taken into consideration. The feed of heat stored in the evaporation chamber or in the components thereof is limited by structural measures and/or a specific material selection, so that the evaporation of the anesthetic required for enriching the gas stream in the evaporation chamber takes place under quasi-adiabatic conditions, especially in the area of surfaces. The evaporation of the anesthetic in the evaporation chamber preferably takes place according to the principle of an at least almost adiabatic surface.

The feed of heat thus ideally takes place exclusively via the heating of the gas stream to be enriched with anesthetic before its entry into the evaporation chamber. The thermal mass of the evaporation chamber, especially of the components enclosing the evaporation area, is thus markedly limited and hence at the same time the mass of the evaporation chamber is considerably reduced compared to prior-art anesthetic evaporators. An unallowable cooling down of the anesthetic evaporator is achieved according to the above-described special embodiment of the present invention by a corresponding heating up of the heating element and thus an additional heating of the gas stream to be enriched with anesthetic.

In a special variant of the present invention, a temperature sensor is provided in the flow direction behind the evaporation chamber for detecting a temperature of the gas enriched with anesthetic, the sensor being connected to the control unit via a data trunk. A corresponding data trunk suitable for data transmission may have a wired or a wireless configuration depending on the application. The temperature sensor is preferably located directly behind the evaporation chamber such that a temperature detection still takes place within the dispensing duct, i.e., before the partial gas stream now enriched with anesthetic flowing through the dispensing duct is again possibly mixed with the partial stream flowing through the fresh gas duct. The temperature sensor thus advantageously detects the temperature of the gas stream or partial gas stream enriched with anesthetic leaving the evaporation chamber.

The actuation of the heating element is preferably carried out by the control unit as a function of the temperature values detected by the temperature sensor and as a function of a vapor pressure curve specific for the particularly used anesthetic. Based on the desired concentration of anesthetic in the gas stream predefined by the anesthetist, the heating element is thus actuated based on need, taking into consideration the vapor pressure curve of the particularly used anesthetic, which vapor pressure curve is stored in the control unit. By providing a temperature sensor behind the evaporation chamber, a closed control circuit is thereby configured, wherein the heat output of the heating element can be set via the control unit as a function of the measured temperature, the desired concentration of the anesthetic and the thermodynamic properties of the particularly used anesthetic and can also be adapted based on need, especially as a function of the progress of the operation and thus of the desired depth of anesthesia.

In a very special embodiment of the present invention, the evaporation chamber has at least two areas, which are preferably arranged in a series behind one another in the flow direction. The at least two areas are preferably configured such that an evaporation takes place at least almost entirely in a first area, while a balancing of the temperature and concentration distribution within the gas stream is achieved in a second area.

Another advantageous configuration of the evaporation chamber provides that an average surface temperature in the evaporation chamber during the operation not exceed a value ranging between 0° C. and 40° C., especially between 30° C. and 40° C. An embodiment, in which the average surface temperature in the evaporation chamber remains below a value of 35° C. during the operation, appears to be especially suitable.

In addition to a device, the present invention also pertains to a method for dispensing an anesthetic into a gas stream, in which a gas to be enriched with anesthetic and coming from a breathing gas or fresh gas source via a gas inlet is heated and fed to an evaporation chamber, in which an anesthetic is added to the gas and in which a gas enriched with the anesthetic is fed via a gas outlet to a patient port. The method according to the present invention is characterized in that the gas to be enriched with the anesthetic is heated before it reaches the evaporation chamber such that a quantity of the anesthetic is fed in the evaporation chamber as a function of at least one status parameter of the gas to be enriched with the anesthetic and/or of the gas at least partially enriched with the anesthetic.

It is thus essential that the gas stream of the gas to be enriched with anesthetic be heated before entry into the evaporation chamber, taking into consideration a command variable, i.e., a desired value for a selected status parameter of the gas stream located in front of, in and/or behind the evaporation chamber. Such a desired value is preferably a gas temperature and/or a material composition of the gas stream.

In a specific embodiment, the heating of the gas stream to be enriched with anesthetic is carried out before entry into the evaporation chamber as a function of a desired concentration of the anesthetic required after leaving the evaporation chamber and/or of a required anesthetic volume flow, i.e., the necessary quantity of anesthetic. Preferably, the quantity of anesthetic in the evaporation chamber is accurately evaporated and added to the gas stream such that the desired concentration and/or the necessary anesthetic volume flow is achieved.

The evaporation of the anesthetic preferably takes place under the conditions of an adiabatic surface in the evaporation chamber, especially in an evaporation area of the evaporation chamber.

In a special variant of the present invention, the evaporation chamber has at least two areas arranged one behind the other in the flow direction, wherein the evaporation of the quantity of anesthetic necessary for enriching the gas stream takes place at least almost completely in a first area, while the second area is used almost exclusively for balancing the temperature of the gas stream as well as mixing the anesthetic with the gas stream. Temperature and/or anesthetic concentration gradients with the gas stream leaving the evaporation chamber are at least largely avoided in this way.

A measurement of the temperature of the partial gas stream enriched with the anesthetic or of the gas stream enriched with the anesthetic advantageously takes place behind the evaporation chamber, wherein the detected temperature values are used as a basis for the actuation of the heating element and thus a closed control circuit is generated. The temperature of the partial gas stream or of the gas stream behind the evaporation chamber hereby preferably represents a control variable, which shall be reached as a manipulated variable by specific actuation of the heat output of the heating element. The control variable is selected as a function of the particularly desired concentration of the anesthetic as well as of the volume flow in this case.

The present invention is explained in greater detail below without limiting the idea of the present invention based on exemplary embodiments with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
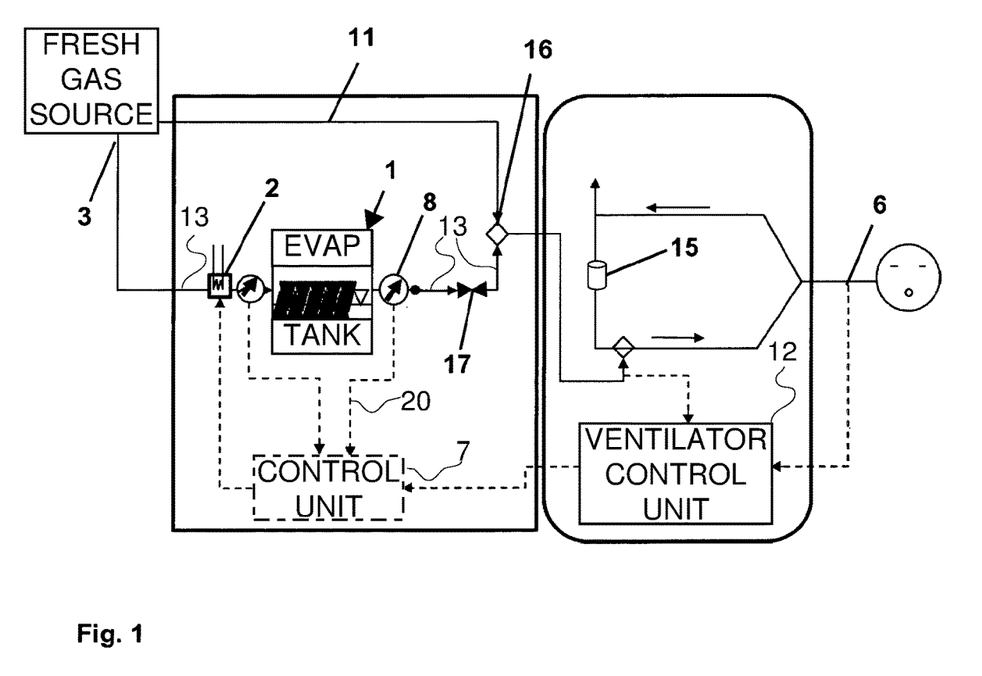
FIG. 1 is a block diagram of the anesthetic-dispensing method configured according to the present invention.

Referring to the drawings, FIG. 1 shows a block diagram of an anesthetic dispenser as configured according to the present invention. Such an anesthetic dispenser is combined with an anesthesia apparatus, the ventilator unit 15 and ventilator control unit 12 of which provides a gas stream enriched with volatile anesthetic as breathing gas stream to a patient via a patient connector 6.

Coming from a fresh gas source 4, fresh gas, which shall be enriched with anesthetic, first reaches the unit for dispensing anesthetic via a gas inlet 3. A fresh gas duct 11 is arranged in terms of flow parallel to the dispensing duct 13, in which a heating element 2 and an evaporation chamber 1 are located. Thus, a first partial gas stream is fed into the dispensing duct 13, while a second partial gas stream flows around the heating element 2 and the evaporation chamber 1. The partial gas stream leaving the fresh gas duct 11 as well as the one leaving the dispensing duct 13 are mixed in a mixing point 16 before reaching the patient connector 6.

According to the exemplary embodiment shown in FIG. 1, the splitting of the fresh gas stream to be enriched with anesthetic into a first and a second partial gas stream occurs within the anesthesia apparatus such that a first partial gas stream, which shall be enriched with anesthetic, and a second partial gas stream, which flows around the heating element 2 and the evaporation chamber, are formed. In terms of the arrangement of the heating element 2, it is selectively possible to integrate this heating element 2 together with the evaporation chamber 1 into a component or into the anesthesia apparatus. In particular, provided that the evaporation chamber 1 including an anesthetic tank 18 of the evaporation chamber is configured as removable from the anesthesia apparatus, it is advantageous when the heating element 2 is arranged in the anesthesia apparatus.

Figure 2:
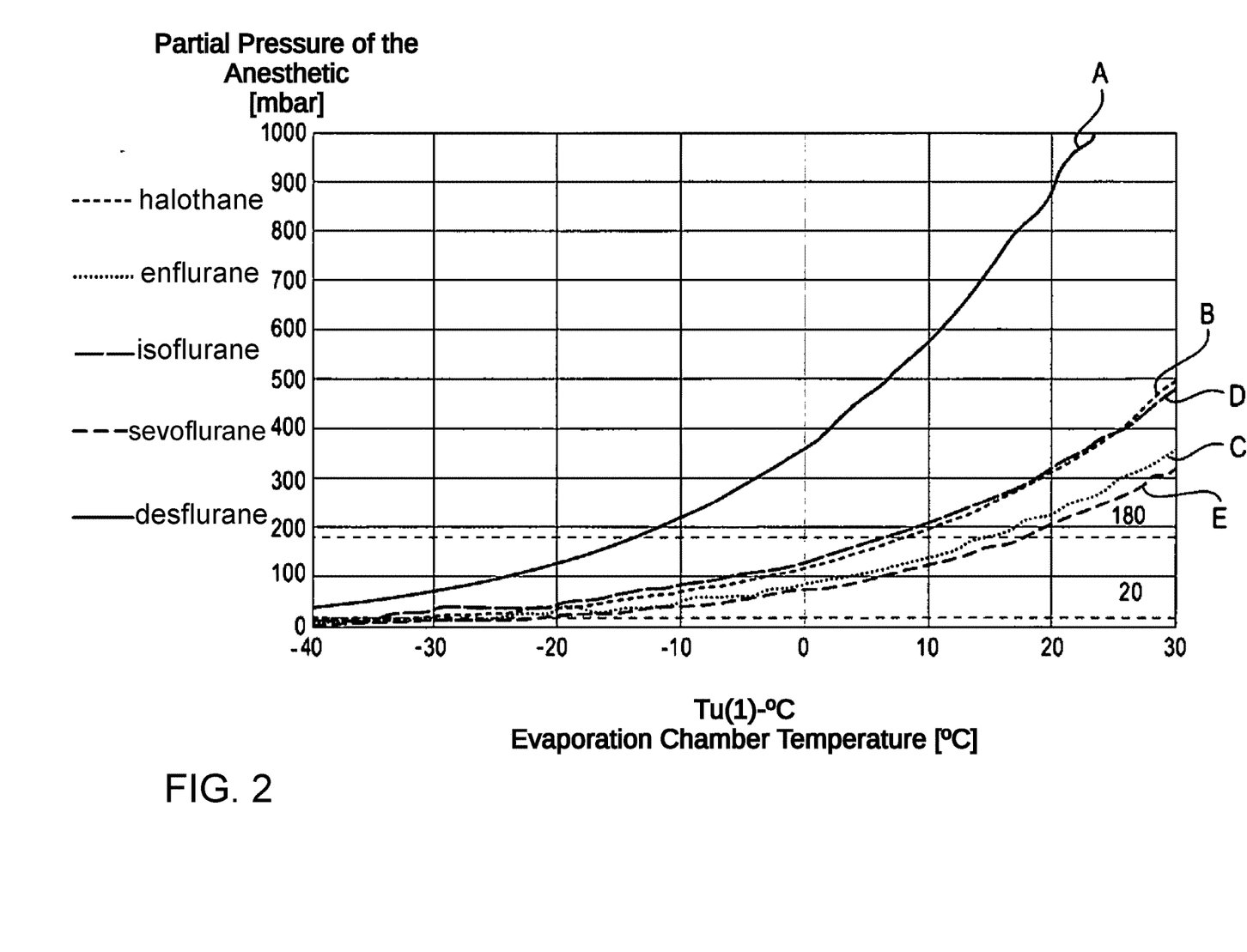
FIG. 2 is a diagram of vapor pressure curves of different volatile anesthetics.

The dispensing duct 13, which will be explained in greater detail below, is located within the area enclosed by a line in FIG. 1. The partial gas stream flowing through the dispensing duct 13 is first fed to a heating element 2. In this heating element 2, the partial gas stream is heated based on need and is subsequently fed to the evaporation chamber 1. A liquid anesthetic is located in a tank 18 within the evaporation chamber 1. In principle, among others, halothane, enflurane, isoflurane, sevoflurane and desflurane are possible as anesthetics, wherein it should be noted in case of using desflurane that this anesthetic is gaseous under normal pressure at ambient temperature and hence should be stored under pressurized conditions. The vapor pressure curves of the above-mentioned anesthetics are shown in FIG. 2.

The gas, which flows into the evaporation chamber 1, reaches an evaporation area 19, in which at least a part of the anesthetic evaporates and is thus mixed with the partial gas stream. The evaporation chamber 1 is hereby preferably configured such that the tank 18 and the evaporation area 19 form a component, which has fastening elements for the detachable fastening of this anesthetic evaporator to the anesthesia apparatus.

The heated gas stream entering the evaporation chamber at least partially discharges heat to the liquid anesthetic, which then evaporates corresponding to the heat input, which depends on the gas volume flow and the temperature difference prevailing between the gas stream temperature and the anesthetic temperature. In order to ensure that the required quantity of anesthetic evaporates and thus the corresponding desired concentration of anesthetic or required anesthetic volume flow is finally contained in the gas stream which is fed to the patient, the heating element 2 is actuated in front of the evaporation chamber 1 such that the correct quantity of anesthetic evaporates within the evaporation chamber 1. The gas enriched with the anesthetic leaves the evaporation chamber 1 via an outlet line, in which a temperature sensor 8 is located for detecting the discharge temperature of the gas enriched with anesthetic. A gate valve 17 is advantageously also located in this area (in dispensing line 13), so that a discharge of anesthetic from the evaporation chamber is reliably prevented for the case, in which no anesthetic is required.

The discharge temperature values that are detected by the temperature sensor 8 located behind the evaporation chamber 1 are likewise transmitted to a control unit 7 via data trunk 20 and finally used as a basis for actuating the heating element 2. The heating element 2 is actuated such that, on the one hand, cooling down effects of the components enclosing the evaporation area 19 of the evaporation chamber 1 are compensated and, on the other hand, the necessary quantity of anesthetic evaporates within the evaporation chamber 1 and is mixed with the gas stream. In addition, the thermodynamic properties, especially the vapor pressure curve, of the particular anesthetic being used are stored for this in the control unit 7. The stored vapor pressure curves represent each the pressure, at which a vapor is in thermodynamic balance with the corresponding, liquid phase of the anesthetic used in a closed system. The vapor pressure increases with increasing temperature and as a material-specific variable is dependent on the particular anesthetic being used. Vapor pressure curves of different anesthetics possible for use are shown in FIG. 2.

Finally, the partial gas stream enriched with anesthetic reaches the mixing point 16, in which it is in turn mixed with the partial gas stream leaving the fresh gas duct 11, so that both partial gas streams are fed immediately after this to the patient via the patient connector 6. The partial gas stream flowing in at the mixing point 16, which leaves the fresh gas duct 11, contains no anesthetic. The partial gas volume flow, which flows through the dispensing duct 13 and the anesthetic concentration determined on the basis of the temperature measurement carried out at the output of the evaporation chamber 1 are multiplied by the specific evaporation enthalpy of the anesthetic used in order to determine the heat output for the heating element 2. In any case, the anesthetic is hereby dispensed into the evaporation chamber 1 such that the gas stream, which is fed to the patient via a patient connector 6, has the desired concentration predefined by the physician and/or the predefined anesthetic volume flow.

The central control unit 7 of the anesthetic dispenser has a user interface, which is connected to this central control unit 7 for data technology and via which the user can input the required parameters, especially the anesthetic used as well as the required desired concentration and/or necessary volume flow of the anesthetic. The concentration of the anesthetic in the dispensing duct 13 behind the evaporation chamber 1 is determined in the control unit 7 using the detected discharge temperatures of the gas and the anesthetic-specific vapor pressure curve as a basis. The required total gas volume as well as the suitable splitting into corresponding partial gas streams is calculated as a function of the concentration and/or quantity of anesthetic carried along with the gas stream determined here as well as the desired concentration and desired volume flow inputted by the user into the control unit 7 and a control signal is generated in order to achieve the corresponding splitting into partial gas streams by means of an electronic control valve 10. In the above-described technical solution, the desired concentration of anesthetic required at the patient connector 6 and/or necessary anesthetic volume flow in the gas stream inputted by the user via the user interface and the corresponding values are stored for data technology in the control unit 7. It is also, however, conceivable that the desired concentration or desired volume flow is not inputted by the user, but rather is determined based on operation-specific and/or patient-specific parameters and subsequently made available to the central control unit 7 of the anesthetic dispenser. A fully automatic control of the anesthetic concentration can be achieved in this case.

The splitting of the fresh gas stream into a first partial gas stream flowing through the dispensing duct 13 and a second partial gas stream flowing through the fresh gas duct 11 arranged parallel thereto is explained below in an example based on special numerical values.

The Partial Pressure of the Anesthetic being used for the temperature prevailing in the Evaporation Chamber can at first be determined by means of the vapor pressure curves shown in FIG. 2 and stored in the central control unit. In this case, for example, a partial pressure of 200 mbar or 200 hPa is obtained for sevoflurane at a temperature of 20° C. Moreover, the required anesthetic partial pressure is determined on the basis of the desired concentration of the anesthetic in the fresh gas stream, which shall be fed to the patient, inputted via a user interface, especially via a touchscreen or a keyboard. For example, an anesthetic partial pressure of 30 mbar is obtained in case of an overall pressure of 1,000 mbar or 1,000 hPa at a desired anesthetic concentration of 3 vol. %. According to the special numerical example selected here, in case of a fresh gas volume flow of 5 L/min fed to the patient for the splitting of the partial gas streams to the dispensing duct 13 or the fresh gas duct 11, this means that a first partial volume flow of 0.751 L/min flows through the dispensing duct 13, where this flow is enriched with the necessary quantity of anesthetic, and a second partial volume flow of 4.249 L/min flows through the fresh gas duct 11.

FIG. 2 shows the vapor pressure curves of the anesthetic currently mainly possible for use. Thus, slightly volatile liquids and gases such as isoflurane, sevoflurane and desflurane are used as anesthetics in anesthesia. Such inhalation anesthetics ensure, on the one hand, extensive analgesia, relax the muscles and lead, on the other hand, to a loss of consciousness and suppress the defensive reflexes. In principle, the method according to the present invention is also suitable for the use of halothane, which has, however, been largely replaced with the three above-mentioned inhalation anesthetics in Europe and in the USA.

Another anesthetic possible, in principle, for use is enflurane, which is a volatile anesthetic from the class of the fluranes similar to halothane. This anesthetic likewise leads to a loss of consciousness and has a muscle-relaxing effect, but leads only to a comparatively minimal suppression of pain and hence is still only used very rarely.

Figure 3:
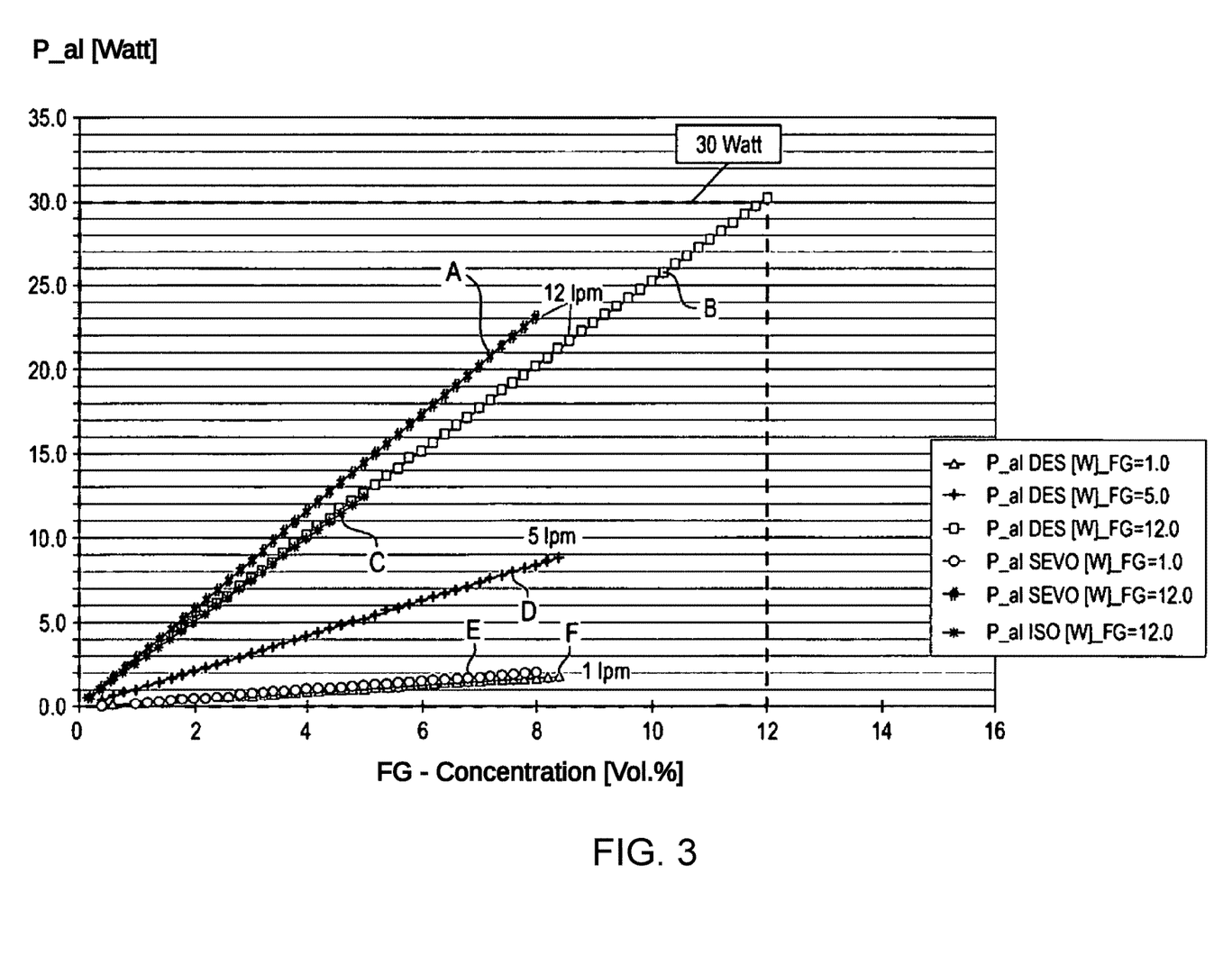
FIG. 3 is a graphic diagram of the heat outputs needed in different use conditions of a heating element arranged according to the present invention.

The vapor pressure curves of desflurane (A), halothane (B), enflurane (C), isoflurane (D), as well as sevoflurane (E) in a temperature range of −40° C. to +30° C. and a pressure range between 0 mbar and 1,000 hPa are shown in FIG. 3 one above the other in this connection. Desflurane is characterized here in that it changes over into the gaseous state at ambient temperature and ambient pressure. For this reason, desflurane (A) is usually pressurized and thus stored in a liquid aggregate state.

FIG. 3 shows, in an example, various heat outputs for different operating states of the anesthetic evaporator configured according to the present invention in relation to the use of different anesthetics and to the setting of various desired concentrations (liters per minute (1 pm)). In this case, at least one correction factor, which depends on the structural configuration of the evaporation chamber 1, especially of the evaporation area 19, and on the technical configuration of the heating element 2, is included in the heat output calculation within the control unit. Thus, the thermal efficiency of the heating element 2 as well as of the evaporation area of the evaporation chamber 1 have a direct effect on the thermal efficiency of the anesthetic evaporator.

Figure 4:
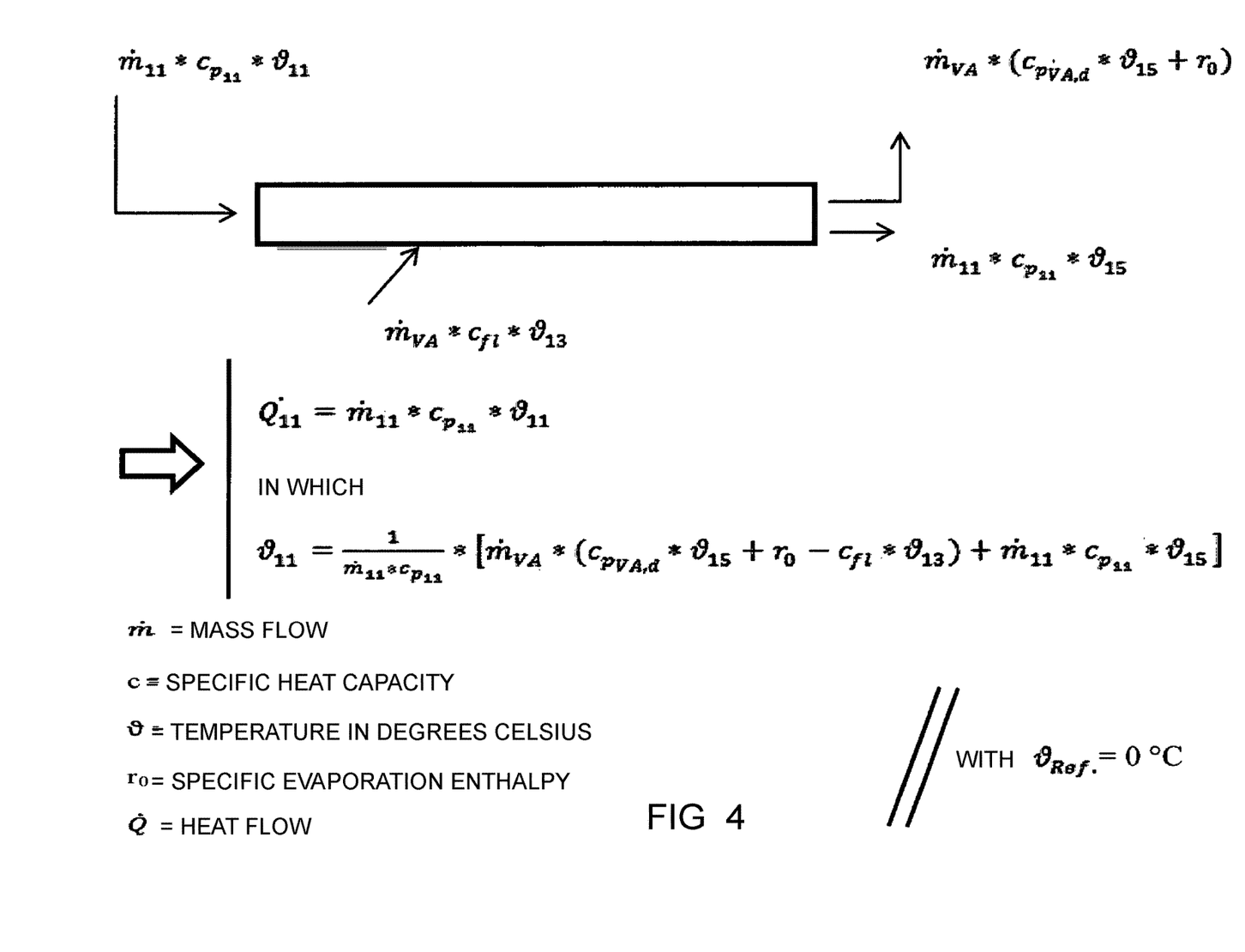
FIG. 4 is a graphic diagram of the energy balance in relation to the evaporation chamber.

The energy balance of the evaporation chamber, wherein the evaporation chamber 1 is regarded thermodynamically as a heat exchanger, is graphically shown in FIG. 4.

Via the fresh gas stream or fresh gas partial stream heated in the heating element 2, heat which can be used for evaporation of the anesthetic is fed to the evaporation chamber 1, which heat depends on the gas volume flow or gas mass flow, the specific heat capacity and the temperature difference between the temperature of the entering gas stream and the temperature of the anesthetic in the evaporation chamber 1. This heat is used for evaporation of the particularly required quantity of anesthetic, so that the temperature of the gas stream cools off again corresponding to the anesthetic-specific evaporation enthalpy. The gas stream leaving the evaporation chamber 1 can now be considered thermodynamically to be a gas stream, which is composed of a fresh gas stream, on the one hand, and an anesthetic stream, on the other hand. Based on this consideration, a heat balance, which takes into consideration, on the one hand, the mass flow of the fresh gas, its specific heat capacity as well as the temperature difference between the temperature of the gas stream flowing into the evaporation chamber 1 and the temperature of the gas stream flowing out of the evaporation chamber 1 and, on the other hand, the mass flow of the evaporation anesthetic, its specific heat capacity and in turn the temperature difference of the gas stream, can be established for the gas stream enriched with anesthetic. The heat which is required to evaporate the required quantity of anesthetic can be determined based on this heat balance, taking into consideration the required desired concentration of the anesthetic used or of the required anesthetic volume flow, the temperature detected behind the evaporation chamber 1 and the vapor pressure curve of the anesthetic. Taking into consideration the thermal efficiency of the evaporation chamber 1 and the efficiency of the heating element 2, the required heat output that is required in the heating element 2 via the central control unit is obtained therefrom.

It is essential to the technical solution according to the present invention that the anesthetic dispenser not require a measurement of the anesthetic concentration either at the input or at the output, since the concentration at the output can be determined on the basis of the vapor pressure curve and the evaporation chamber configuration.

While specific embodiments of the invention have been shown and described in detail to illustrate the application of the principles of the invention, it will be understood that the invention may be embodied otherwise without departing from such principles.

The invention claimed is:

1. A device for dispensing an anesthetic into a gas stream, the device comprising:
    a gas inlet configured to receive fresh gas;
    a heating element receiving fresh gas from said gas inlet, said heating element being configured to heat the received fresh gas;
    an evaporation chamber receiving the heated fresh gas from said heating element, said evaporation chamber having a tank for liquid anesthetic and having an evaporation area configured to evaporate at least partially the liquid anesthetic;
    a gas outlet configured to receive anesthetic enriched gas from said evaporation chamber, and deliver the anesthetic enriched gas to a patient;
    a controller connected to said heating element to selectively evaporate a partial amount of anesthetic from the anesthetic in said tank to be dispensed into the gas stream, said controller selectively controlling a concentration of anesthetic in the anesthetic enriched gas by actuating said heating element.

2. The device in accordance with claim 1, wherein:
    said controller actuates said heating element as a function of a desired concentration of anesthetic in the anesthetic enriched gas.

3. The device in accordance with claim 2, wherein:
    said controller actuates said heating element to feed an amount of heat to the fresh gas to have the fresh gas enriched with a desired amount of anesthetic.

4. The device in accordance with claim 3, wherein:
said controller has an interface receiving a value representing a desired amount of anesthetic to be delivered to the patient, said controller controlling said heating element to selectively heat the received fresh gas as a function of the value representing the desired amount of anesthetic to be delivered to the patient.

5. A device for dispensing an anesthetic into a gas stream, the device comprising:
a gas inlet configured to enrich gas with anesthetic, the gas coming from a gas source;
a gas outlet configured to enable gas enriched with the anesthetic to flow to a patient port;
an evaporation chamber configured to dispense the anesthetic into the gas stream;
a heating element, for heating the gas and arranged in a flow direction of the gas between the gas inlet and the gas outlet, wherein the heating element is arranged upstream of the evaporation chamber in the flow direction of the gas; and
a controller configured to actuate the heating element such that heat is fed to the gas to be enriched with anesthetic for partial evaporation of the anesthetic located in the evaporation chamber as a first function of one of:
a required desired concentration of the anesthetic in the gas after leaving the evaporation chamber, or a necessary anesthetic volume flow, or the required desired concentration of the anesthetic in the gas after leaving the evaporation chamber and of the necessary anesthetic volume flow;
and as a second function of one of:
at least one status parameter of the gas to be enriched with the anesthetic, or the gas at least partially enriched with the anesthetic, or the at least one status parameter of the gas to be enriched with the anesthetic and the gas at least partially enriched with the anesthetic.

6. The device in accordance with claim 5, wherein the at least one status parameter is a temperature and/or a material composition of the gas stream.

7. The device in accordance with claim 5, wherein the evaporation chamber has a tank for liquid anesthetic and an evaporation area, in which liquid anesthetic at least partially evaporates.

8. The device in accordance with claim 7, wherein the evaporation chamber and the tank are configured as one component.

9. The device in accordance with claim 5, further comprising the device being detachably connected to an anesthesia apparatus.

10. The device in accordance with claim 5, wherein the heating element is able to be actuated such that a temperature of a chamber wall defining the evaporation chamber in an inward direction is at least almost constant during operation.

11. The device in accordance with claim 5, further comprising:
a data link; and
a temperature sensor, for detecting a temperature of the gas enriched with anesthetic, connected to the control unit via the data link, wherein the temperature sensor is provided downstream of the evaporation chamber in the flow direction, and wherein the heating element is actuated by the control unit as a function of:
temperature values detected by the temperature sensor, and
a vapor pressure curve specific for the anesthetic wherein the vapor pressure curve describes a saturation partial pressure as a function of an evaporation chamber temperature.

12. The device in accordance with claim 5, wherein the evaporation chamber has at least two areas, with anesthetic evaporation taking place at least almost exclusively in one of the two areas.

13. The device in accordance with claim 5, wherein the heating element is actuated such that the gas stream leaving the evaporation chamber is at least almost saturated with anesthetic.

14. The device in accordance with claim 5, wherein the heating element and the evaporation chamber are structurally integrated into one component.

15. A method for dispensing an anesthetic into a gas stream, the method comprising the steps of:
providing an anesthetic dispensing device comprising a gas inlet, a gas outlet, an evaporation chamber, a heating element and a control unit;
heating a gas to be enriched with the anesthetic, the gas coming from a gas source via the gas inlet; and
feeding the heated gas to the evaporation chamber, in which the anesthetic is dispensed into the gas, and in which the gas enriched with the anesthetic is fed to a patient port via the gas outlet, the gas to be enriched with the anesthetic being heated before the gas reaches the evaporation chamber such that a partial quantity of liquid anesthetic in the evaporation chamber is evaporated, the gas to be enriched with the anesthetic is heated as a first function of one of:
a desired concentration of the anesthetic, or an anesthetic volume flow in the gas stream leaving the evaporation chamber, or the desired concentration of the anesthetic and of the anesthetic volume flow in the gas stream leaving the evaporation chamber;
and as a second function of one of:
at least one status parameter of the gas to be enriched with the anesthetic, or the gas at least partially enriched with the anesthetic, or the at least one status parameter of the gas to be enriched with the anesthetic and of the gas at least partially enriched with the anesthetic.

16. The method in accordance with claim 15, wherein the gas to be enriched with anesthetic is heated such that an evaporation of the anesthetic takes place in the evaporation chamber under at least almost adiabatic conditions.

17. The method in accordance with claim 15, wherein the heating of the gas to be enriched with anesthetic takes place such that an average surface temperature in the evaporation chamber is within a range between 0° C. and 50° C. during an operation.

18. The method in accordance with claim 17, wherein the gas stream to be enriched with anesthetic is heated before entry into the evaporation chamber such that the gas stream leaving the evaporation chamber is at least almost saturated with anesthetic.

19. The method in accordance with claim 15, wherein
at least one temperature of the gas stream to be enriched with anesthetic is detected in front of the evaporation chamber, or
one temperature of the gas stream enriched with anesthetic is detected behind the evaporation chamber, or
at least one temperature of the gas stream to be enriched with anesthetic is detected in front of the evaporation chamber and one temperature of the gas stream enriched with anesthetic is detected behind the evaporation chamber;

wherein the gas stream to be enriched with anesthetic is heated as a function of:
   temperature values detected by a temperature sensor, and
   a vapor pressure curve specific for the anesthetic;
wherein the vapor pressure curve describes a saturation partial pressure as a function of an evaporation chamber temperature.

20. A device for dispensing an anesthetic into a gas stream, the device comprising:

a gas inlet configured to receive fresh gas;

a heating element receiving the fresh gas from said gas inlet, said heating element being configured to heat the received fresh gas;

an evaporation chamber receiving the heated fresh gas from said heating element, said evaporation chamber having a tank for liquid anesthetic and having an evaporation area configured to evaporate at least partially the liquid anesthetic;

a gas outlet configured to receive anesthetic enriched gas from said evaporation chamber, and deliver the anesthetic enriched gas to a patient;

a controller connected to said heating element to selectively evaporate a portion of the liquid anesthetic in said tank, said tank holding an amount of liquid anesthetic exceeding an amount needed by the patient, said controller controlling a concentration of anesthetic in the anesthetic enriched gas by actuating said heating element, the portion evaporated under control of the controller being selected to correspond to a desired concentration of anesthetic to be delivered to the patient.

* * * * *